United States Patent
Zhou et al.

(10) Patent No.: US 10,768,453 B2
(45) Date of Patent: Sep. 8, 2020

(54) DEVICES FOR CLEANING CONTACT LENSES

(71) Applicant: Bolb Inc., San Jose, CA (US)

(72) Inventors: Ling Zhou, Dublin, CA (US); Jianping Zhang, Arcadia, CA (US); Ying Gao, Fremont, CA (US)

(73) Assignee: Bolb Inc., Livermore, CA (US)

( * ) Notice: Subject to any disclaimer, the term of this patent is extended or adjusted under 35 U.S.C. 154(b) by 185 days.

(21) Appl. No.: 15/640,580

(22) Filed: Jul. 3, 2017

(65) Prior Publication Data

US 2019/0004339 A1    Jan. 3, 2019

(51) Int. Cl.
*A61L 12/06* (2006.01)
*B08B 3/12* (2006.01)
*G02C 13/00* (2006.01)

(52) U.S. Cl.
CPC .......... *G02C 13/008* (2013.01); *A61L 12/063* (2013.01); *B08B 3/12* (2013.01)

(58) Field of Classification Search
CPC ....... B08B 3/12; B08B 7/0057; A61L 12/063; A61L 12/026; A61L 12/06; G02C 13/008; A45C 11/005; A45C 11/043
USPC ..................................................... 422/20, 24
See application file for complete search history.

(56) References Cited

U.S. PATENT DOCUMENTS

| | | | |
|---|---|---|---|
| 5,120,499 A * | 6/1992 | Baron | A61L 12/026 250/455.11 |
| 5,144,144 A * | 9/1992 | Borovsky | A61L 12/063 250/455.11 |
| 5,965,249 A | 10/1999 | Sutton et al. | |
| 6,070,734 A | 6/2000 | Hunt et al. | |
| 8,158,961 B2 | 4/2012 | Merkle | |
| 9,282,796 B2 | 3/2016 | Pugh et al. | |
| 2005/0028848 A1* | 2/2005 | Lai | B08B 3/12 134/184 |
| 2009/0216299 A1 | 8/2009 | Dantus | |
| 2010/0326484 A1* | 12/2010 | Wu | A61L 2/24 134/56 R |
| 2011/0284396 A1* | 11/2011 | Pugh | A45C 11/005 206/5.1 |
| 2012/0138819 A1 | 6/2012 | Pugh et al. | |

\* cited by examiner

*Primary Examiner* — Marc Lorenzi
(74) *Attorney, Agent, or Firm* — Patent Office of Dr. Chung Park (57) ABSTRACT

A device for cleaning a contact lens includes a lid, a base portion and a drawer unit detachably coupled to the base portion. The drawer unit includes a container holding a volume of fluid therein. The device also includes a vibration generator for generating an oscillatory motion on the container, where the oscillatory motion induces turbulence in the fluid with sufficient force to dislodge deposits from a lens immersed in the fluid. The device also includes a circuit board secured to the base portion and a light source for generating radiation to disinfect the dislodged deposits in the fluid. A suspension secures the light source to the circuit board and a resonance frequency of the suspension is offset from a frequency of the oscillatory motion.

13 Claims, 9 Drawing Sheets

DEVICES FOR CLEANING CONTACT LENSES

BACKGROUND

A. Technical Field

The present invention relates to devices for contact lens care system, and more particularly, to devices that clean and disinfect contact lenses in one integrated unit.

B. Background of the Invention

Contact lenses have become widely used, and various lens materials and techniques for cleaning and sterilizing contact lenses have been developed. Typically, contact lenses are fragile and collect surface contaminants. Surface contaminants on contact lenses can come from external sources such as dirty fingers, air borne particles or from eye discharge that can consist of protein deposits or lipid. Surface contaminants may also include bacterial and fungal deposits. The surface contaminants cause ophthalmic diseases and diminish visual acuity if they are not properly removed before the contact lenses are reinserted into the user's eyes.

One approach to remove the surface contaminants without user touch is using a liquid container coupled to a source of vibration. For instance, U.S. Pat. Nos. 5,144,144 and 9,282,796 disclose devices for cleaning contact lenses. As described in '144 patent, a contact lens and lens cleaning fluid are filled in the cleaning chamber, and the vibrator generates whirlpool wave in the container. The turbulent waves rinse the surface contaminants on the contact lenses. Then, the contaminants in the cleaning fluid and on the lenses are sterilized by a UV light source. In 796 patent, a contact lens is directly exposed to UV light source for sterilization.

Some consumers prefer smaller size lens cleaning devices so that the devices can be easily carried. As the lens cleaning device becomes more compact, the components of the device are arranged in close proximity, posing several problems: (1) damage to components, such as UV light source, UV light driver electronics and electrical contacts, due to the vibrational motion of the vibrator and (2) damage to contact lenses due to UV light.

As the spacing between components of the device shrinks, the intensity of the vibrational motion transferred from the vibrator to other components increases. The transferred vibrational motion can inflict mechanical damages to the components. As such, there is a need for a damping mechanism that can reduce the intensity of transferred vibrational motion and/or isolate the components from the vibrational motion.

In general, after an extended period of use, the contact lenses may become cloudy due to several factors, resulting in blurry/hazy vision. One of the factors that cause clouding of the contact lenses is the UV light that is used to inactivate the pathogens on the contact lenses. Contact lenses, which may be made of plastic polymers, may degrade from direct exposure to the UV light over an extended period of time. Some contact lens manufacturers cure polymer material by UV light to form the contact lenses. Since vast majority of lens polymers are UV absorbing materials, the contact lenses may change their color, stiffness or other properties when they are directly exposed to UV light having an excessive intensity, especially if the UV light is in the C band.

Furthermore, as the size of the device decreases, the distance between the UV light source and the contact lens decreases, increasing the intensity of UV light impinging on the contact lenses. Some conventional devices, such as the device disclosed in 796 patent, use optical components to focus the UV light directly onto the contact lenses. Because the UV light beyond a certain threshold level may damage the contact lenses, a new mechanism is required to moderate or prevent the direct UV exposure to the lens, while maintain or enhance UV dose received by the cleaning solution that contains contaminants rinsed off from the lens.

As such, there is a need for compact lens cleaning devices that can effectively remove and disinfect lens contaminants on the lens surface while the components of the devices are protected from the damages due to excessive vibrational motion and overexposure to UV light.

SUMMARY OF THE DISCLOSURE

In one aspect of the present invention, a device for cleaning a contact lens includes: a container having a chamber for holding a volume of fluid therein; a vibration generator for generating an oscillatory motion within the container, the oscillatory motion inducing turbulence in the volume of fluid with sufficient force and duration to dislodge deposits from a lens immersed in the volume of fluid; a light source for generating radiation to disinfect the dislodged deposits in the fluid; a circuit board having electronic circuits for controlling the vibration generator and light source; and a suspension for securing the light source to the circuit board, a resonance frequency of the suspension being offset from a frequency of the oscillatory motion.

In another aspect of the present invention, a device for cleaning a contact lens includes: a container having a chamber for holding a volume of fluid therein; a vibration generator for generating an oscillatory motion on the container, the oscillatory motion inducing turbulence in the volume of fluid with sufficient force and duration to dislodge deposits from a lens immersed in the volume of fluid; a light source for generating radiation to disinfect the dislodged deposits in the fluid; and a window assembly including a window and a window holder and detachably secured to the container to form an enclosed space for the fluid; the window being formed of material that is transparent to the radiation and having an element that diffuses or redirects the radiation.

In yet another aspect of the present invention, a device for cleaning a contact lens includes: a housing including a lid and a base portion; a drawer unit detachably coupled to the base portion and including a container that has a chamber for holding a volume of fluid therein; a vibration generator for generating an oscillatory motion on the container, the oscillatory motion inducing turbulence in the volume of fluid with sufficient force and duration to dislodge deposits from a lens immersed in the volume of fluid; a circuit board secured to the base portion; a light source for generating radiation to disinfect the dislodged deposits in the fluid; and a suspension for securing the light source to the circuit board, a resonance frequency of the suspension being offset from a frequency of the oscillatory motion.

BRIEF DESCRIPTION OF THE DRAWINGS

References will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

DETAILED DESCRIPTION OF THE PREFERRED EMBODIMENTS

In the following description, for the purposes of explanation, specific details are set forth in order to provide an understanding of the disclosure. It will be apparent, however, to one skilled in the art that the disclosure can be practiced without these details. One skilled in the art will recognize that embodiments of the present disclosure, described below, may be performed in a variety of ways and using a variety of means. Those skilled in the art will also recognize additional modifications, applications, and embodiments are within the scope thereof, as are additional fields in which the disclosure may provide utility. Accordingly, the embodiments described below are illustrative of specific embodiments of the disclosure and are meant to avoid obscuring the disclosure.

A reference in the specification to "one embodiment" or "an embodiment" means that a particular feature, structure, characteristic, or function described in connection with the embodiment is included in at least one embodiment of the disclosure. The appearance of the phrase "in one embodiment," "in an embodiment," or the like in various places in the specification are not necessarily all referring to the same embodiment.

Figure 1:
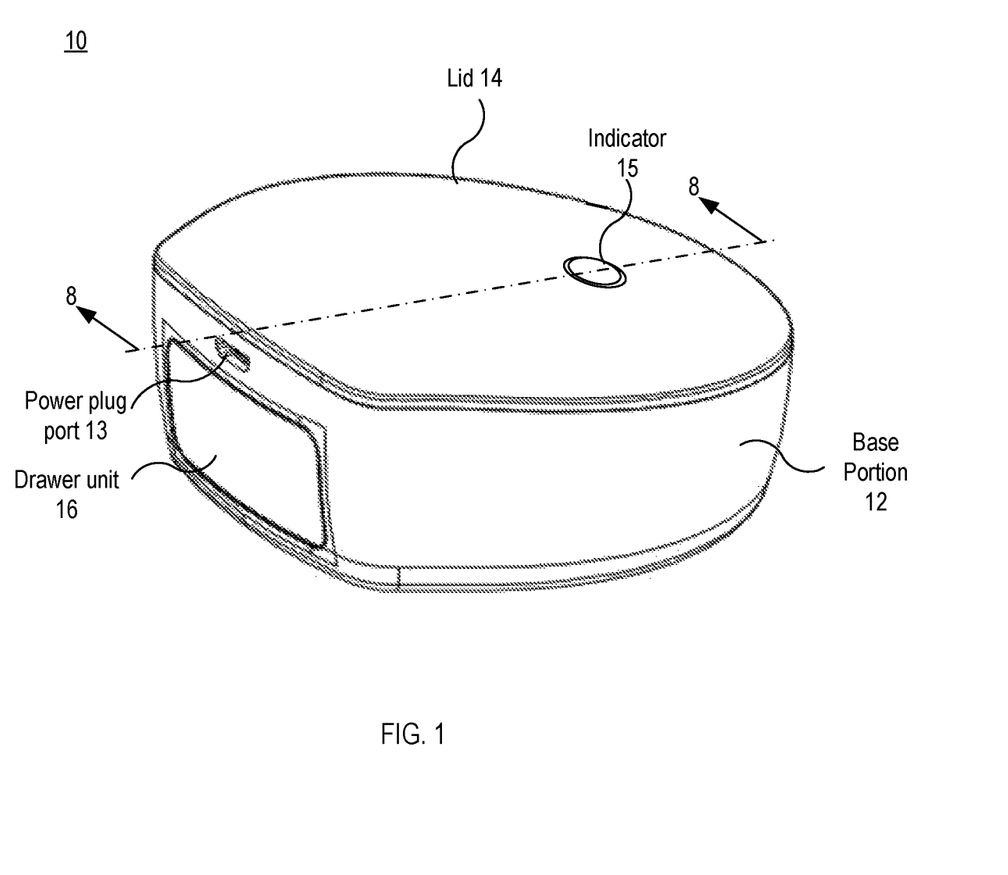
FIG. 1 shows a perspective view of a device for cleaning and disinfecting contact lenses according to embodiments of the present disclosure.
Figure 2:
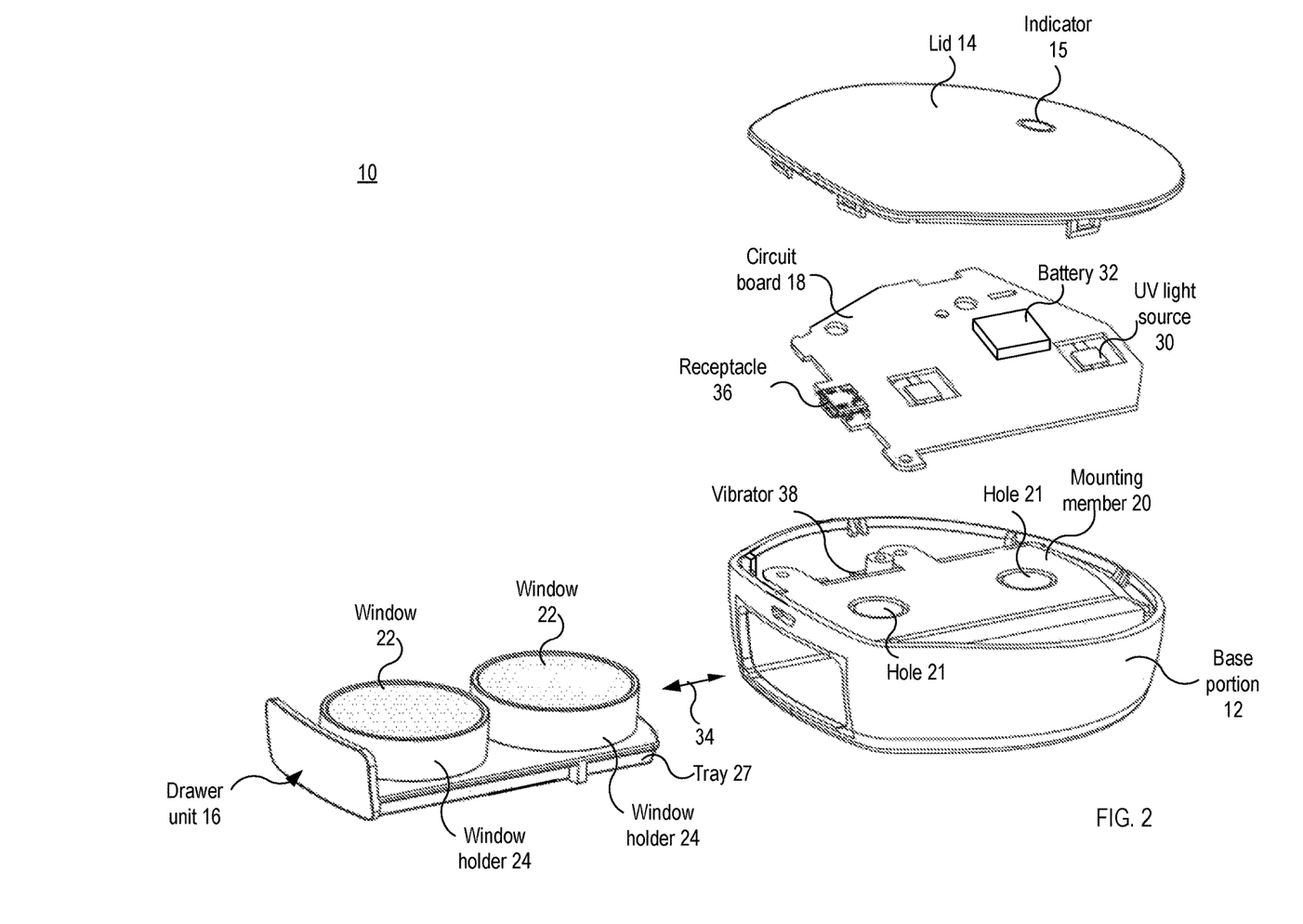
FIG. 2 shows an exploded perspective view of the device in FIG. 1.

FIG. 1 shows a perspective view of a device 10 for cleaning and sterilizing/disinfecting contact lenses according to embodiments of the present disclosure. FIG. 2 shows an exploded perspective view of the device 10 in FIG. 1.

Figure 3:
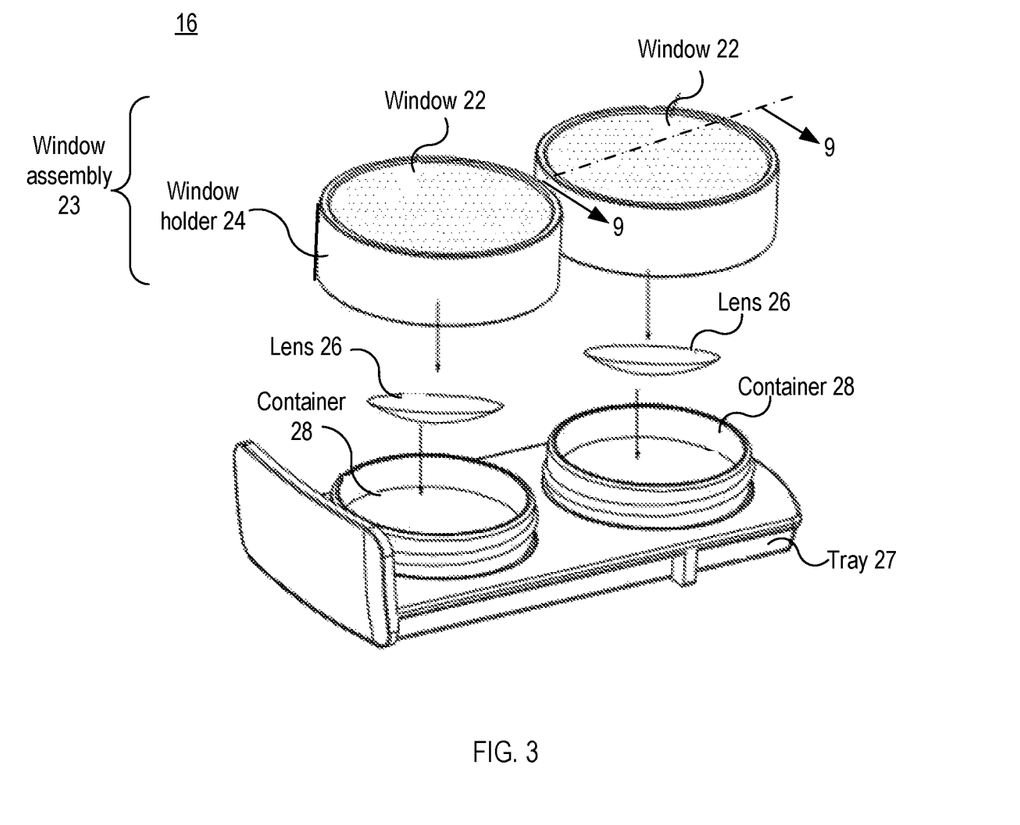
FIG. 3 shows an exploded view of the drawer unit in FIG. 2.
Figure 8:
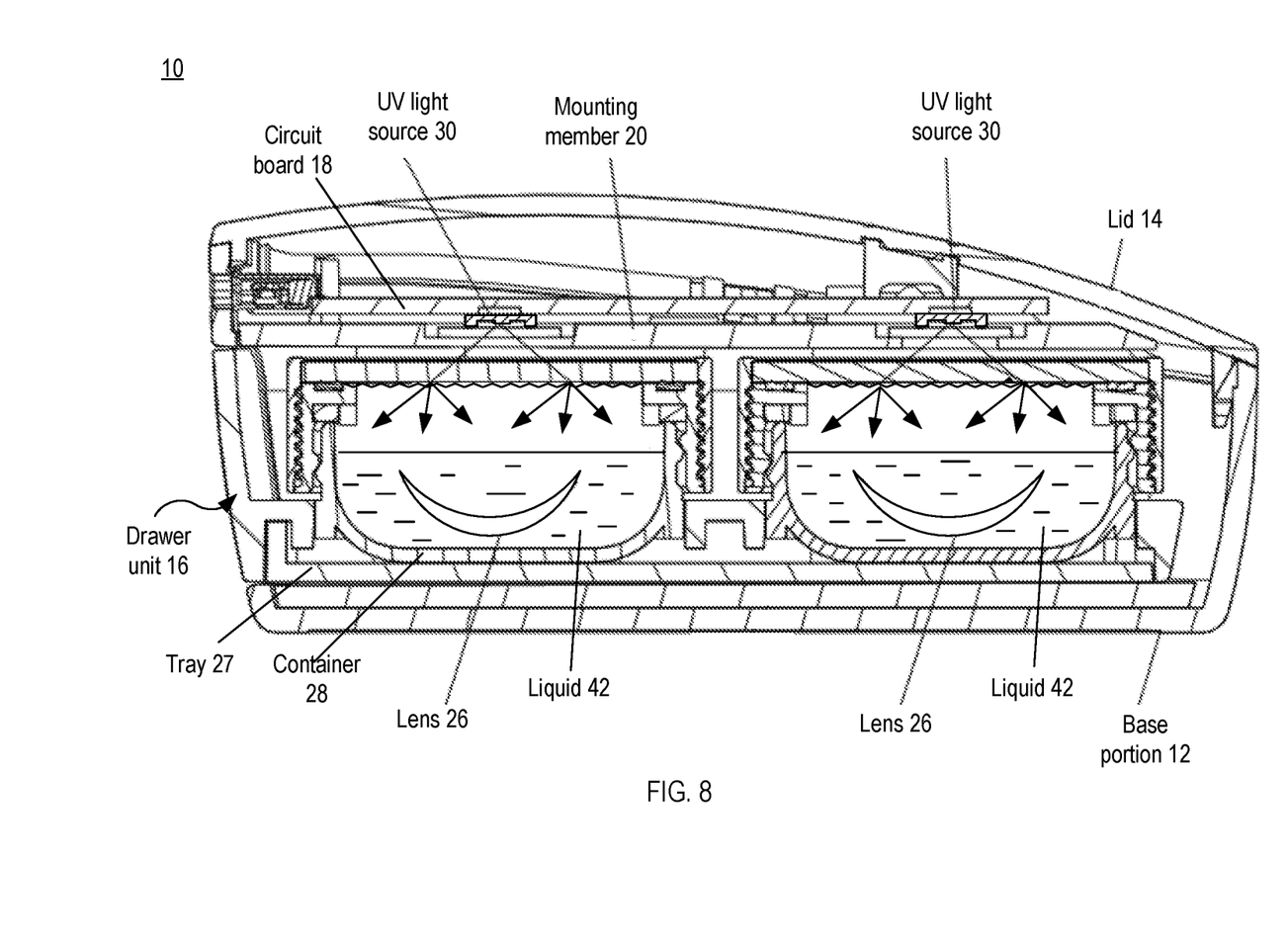
FIG. 8 shows a cross sectional view of the device in FIG. 1, taken along the direction 8-8 according to embodiments of the present disclosure.

FIG. 3 shows an exploded view of the drawer unit 16 in FIG. 2. FIG. 8 shows a cross sectional view of the device 10, taken along the direction 8-8 in FIG. 1. As depicted, the device 10 may include: a lid 14; a drawer unit 16 including liquid containers (or shortly containers) 28 mounted on a tray 27, windows 22 and window holders 24; and a base portion 12 for accommodating the drawer unit 16, a circuit board 18 and a mounting member 20. The drawer unit 16 may be detachably engaged with the base portion 12 so that the user may mount (or dismount) the drawer unit 16 onto the base portion 12, as indicated by an arrow 34, to access the containers 28.

In embodiments, the indicator light 15 may be formed on the lid 14, and provide status information of the device 10 to the user. For instance, the indicator light 15 may be lit during a cleaning cycle and turned off when the cleaning cycle is over. In embodiments, the indicator light 15 may use different colors or texture or both to indicate various operational status or battery status of the device 10. In embodiments, the indicator light 15 may also operate as a turn on/off switch (button), i.e., the user touches the indicator light 15 to start/stop the cleaning cycle. In embodiments, the indicator light 15 may be also used as a user button for other built-in functions of the devices 10, such as ejecting the drawer unit 16 from the base portion 12. It is noted that other suitable type and/or number of buttons/switches/indicators may be included in the lid 14.

In embodiments, the circuit board (or, equivalently a board member) 18 may have electronic components for operating the device 10 and include conductive traces and pads formed on a substrate. As described below in conjunction FIG. 13, the circuit board 18 may include various electrical circuits/drivers for controlling various components of the device 10.

In embodiments, the battery 32, which may be a lithium battery, may be mounted on the circuit board 18 and provide electrical power to the indicator 15, UV light source 30, vibrator 38 and other electrical circuits/drivers on the circuit board 18. In embodiments, the user may insert an input power plug into the power plug port 13, and the conductive tip portion of the power plug may be engaged in the receptacle 36 to thereby provide electrical power to the circuit board 18 and charge the battery 32.

In embodiments, the window assembly 23 may include windows 22 and window holders 24. In embodiments, each of the window holders 24 may have a threaded inner wall while the corresponding container 28 may have a threaded outer wall so that the user may turn the window holder 24 relative to the container 28 to firmly and detachably lock (or unlock) the window holder 24 to (or from) the container 28. The window holder 24 and the container 28 may form an enclosed and water-tight space where the liquid 42 and the lens 26 are confined therewithin.

To clean the lenses 26, the user may take the drawer unit 16 out of the base portion 12, fill the lens cleaning fluid (or liquid) 42 in the containers 28, place the lenses 26 in the cleaning fluid (or liquid) 42, securely lock the window holders 24 to the containers 28, and engage the drawer unit 16 into the base portion 12. Then, the user may start the cleaning cycle. Upon completing the cleaning cycle, the user may take the drawer unit 16 out of the base portion 12 and take the lenses 26 from the containers 28.

In embodiments, the vibrator (or, vibration generator) 38 may be secured to the mounting member 20 that is secured to the base portion 12. The vibrator 38 may be controlled by a vibrator driving circuit that is included in the circuit board 18 and set the containers 28 in oscillatory motion during the cleaning cycle. The oscillatory motion (or shortly, oscillation or vibration) may create waves in the containers 28 during the cleaning cycle. The turbulent waves may rinse through, clean, and dislodge deposits from the lenses 26 immersed in the fluid 42. Hereinafter, the term deposits collectively refer to particles, virus/mold/bacteria, films and surface contaminants on contact lenses.

In embodiments, the UV light source 30 may generate UV light that disinfect the liquid 42 and lenses 26 during the cleaning cycle. The deposits dislodged by the wave action may be disinfected by the UV light from the UV light source 30. It is noted that the UV light source 30 may be replaced by other suitable disinfecting light sources, i.e., the light source 30 may be any suitable radiation source that generates radiation for disinfecting the dislodged deposits. The UV light emitted by the UV light source 30 may pass through the holes 21 formed in the mounting member 20 and the windows 22, where the windows 22 may be formed of material that is transparent to the UV light, such as quartz and sapphire. In embodiments, the UV light source 30 may include a UV light emitting diode (UV LED) and the wavelength of the UV light source may be in the range of 250-300 nm.

In embodiments, the light source 30 may emit light in either continuous mode or pulse (or flash) mode. By operating the light source 30 in the pulse mode, the lifetime of the light source may be extended and the irradiance of the light may be increased. In embodiments, the electric circuit (such as 118 in FIG. 13) for driving the light source 30 may control the widths and repetition frequencies of the emitted light pulses. For instance, in embodiments, the pulse width may range from 1 msec to a few seconds and the repetition rate may range from a few tens of Hz to a few KHz.

Figure 4:
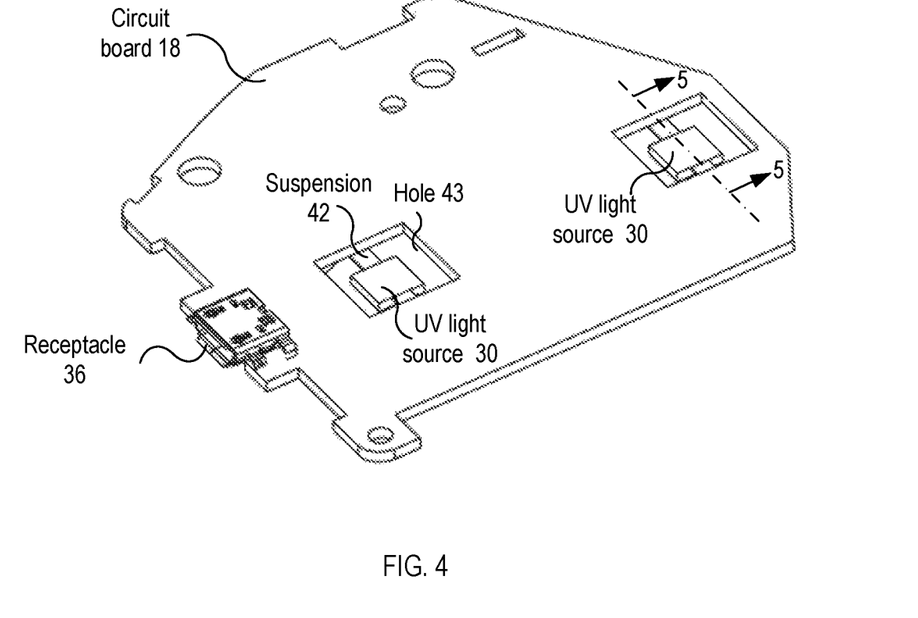
FIG. 4 shows an enlarged view of the circuit board in FIG. 2
Figure 5:
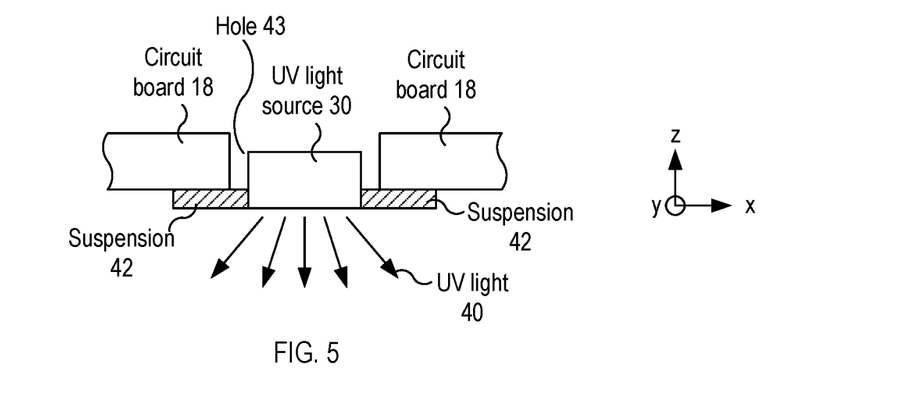
FIG. 5 shows a cross section view of a UV light source, taken along the direction 5-5 in FIG. 4.

The UV light source 30 may include electrical components that may be damaged if they are not protected from the oscillation/vibration generated by the vibrator 38. FIG. 4 shows an enlarged view of the circuit board 18 in FIG. 2. FIG. 5 shows a cross section view of the UV light source 30, taken along the direction 5-5 in FIG. 4. As depicted, the UV light source 30 may be mounted on the circuit board 18 by suspensions 42. In embodiments, the suspensions 42 may be formed of flexible material to prevent the oscillatory motion of the circuit board 18 from being transmitted to the UV light source 30, i.e., the suspensions 42 may isolate the UV light source from the vibration generated by the vibrator 38 and/or damp the vibrational motion of the UV light source 30. In embodiments, the suspensions 42 not only provide mechanical strength to secure the UV light source 30 to the circuit board 18 but also protect the UV light source 30 from the oscillation/vibration.

In embodiments, the circuit board 18 may include a UV light source driving circuit (118 in FIG. 13) that provides electrical power and control signals to the UV light source 30 via the suspensions 42. In embodiments, the suspensions 42 may include electrically conducting wires so that the UV light source 30 is electrically connected to the circuit board 18.

Figure 6A:
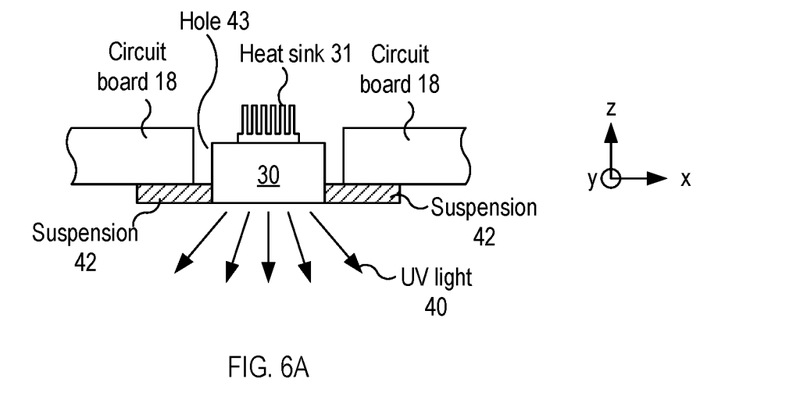
FIG. 6A shows a cross section view of a UV light source according to embodiments of the present disclosure.

FIG. 6A shows a cross section view of a UV light source according to embodiments of the present disclosure. As depicted, a heat sink 31 may be attached to a top surface of the UV light source 30 by a suitable adhesive material, such as thermal glue with high thermal conductivity, where the heat sink 31 may extract heat energy from the UB light source 30 and discharge the heat energy to the air. In embodiments, the heat sink 31 may be formed of material having high thermal conductivity, such as copper, and include cooling fins.

Figure 6B:
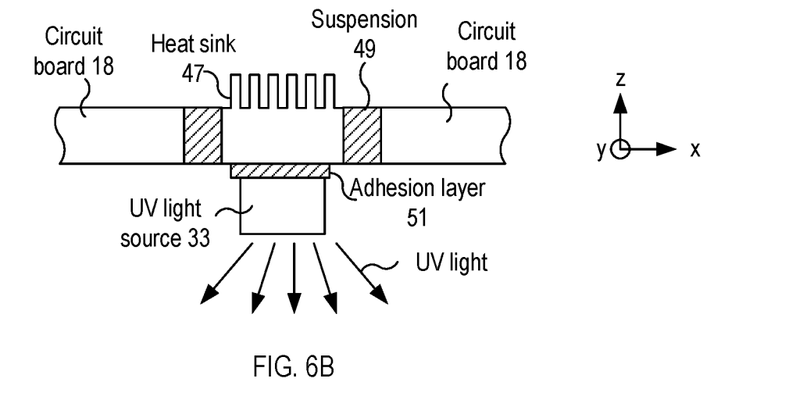
FIG. 6B shows a cross section view of a UV light source according to embodiments of the present disclosure.

FIG. 6B shows a cross section view of a UV light source according to embodiments of the present disclosure. As depicted, a heat sink 47 may be secured to the circuit board 18 by the suspensions 49, and the UV light source 33 may be secured to the bottom surface of the heat sink by an adhesion layer 51. In embodiments, the adhesion layer 51 may be formed of thermal glue so that the heat energy generated by the UV light source 33 may be efficiently conducted to the heat sink 47 through the adhesion layer 51. In embodiments, the heat sink 47 may extract heat energy from the UV light source 33 and discharge the heat energy to the air. In embodiments, the heat sink 47 may be formed of material having high thermal conductivity, such as copper, and include cooling fins.

In embodiments, the UV light source 30 (or 33) in FIGS. 5, 6A and 6B may include delicate components and circuits for generating light, such as LED and LED driver electronics. In embodiments, the suspensions 42 (or 49) may be designed to protect the UV light source from the damage due to the vibrational motion of the vibrator 38. In FIGS. 5, 6A and 6B, the suspensions 42 (or 49) may have spring constants $k_x$, $k_y$ and $k_z$ for the motions along the x, y and z axes. For each spring constant, e.g., $k_x$, the resonance frequency, e.g. $f_x$, may be represented by an equation:

$$f_x = \frac{1}{2\pi}\sqrt{\frac{k_x}{m}}$$

where m is the mass of the components supported by the suspensions. In FIG. 5, m is the mass of the UV light source 30. In FIG. 6A, m is the total mass of the UV light source 30 and the heat sink 31. Similarly, in FIG. 6B, m is the total mass of the UV light source 33, adhesion layer 51 and the heat sink 47.

If one or more of the resonance frequencies $f_x$, $f_y$ and $f_z$ match the vibrational frequency of the vibrator 38, the suspensions 42 (or 49) may respond at greater amplitude to the vibrational motion of the vibrator 38, resulting in damage to the suspensions and the UV light source. Since the spring constants of the suspensions 42 (or 49) may be determined by the material and the dimension of the suspensions, the material and dimension of the suspensions 42 (or 49) may be determined so that the resonance frequencies $f_x$, $f_y$ and $f_z$ are offset from the vibrational frequency of the vibrator 38. In embodiments, the vibrational motion of the vibrator 38 may be transferred to the circuit board 18, causing the circuit board 18 to vibrate at the vibrational frequency of the vibrator 38. By offsetting the resonance frequencies $f_x$, $f_y$ and $f_z$ from the vibrational frequency of the vibrator 38, the vibrational motion of the UV light source 30 (or 33) may be damped by the suspensions 42 (or 49), i.e., the intensity of the vibrational motion transferred from the circuit board 18 to the UV light source 30 (or 33) may be reduced.

Figure 7:
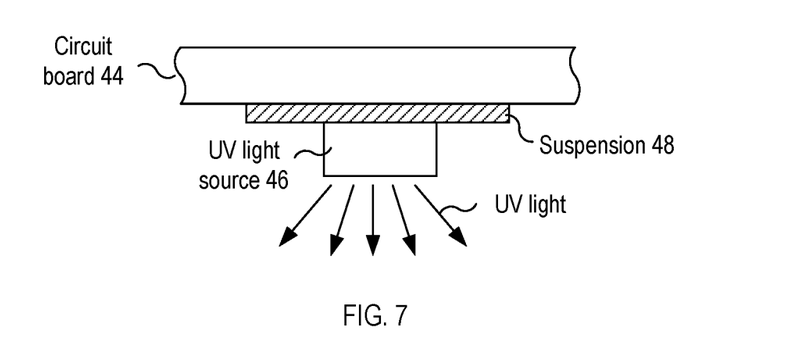
FIG. 7 shows a cross section view of a UV light source according to embodiments of the present disclosure.

In FIGS. 5, 6A and 6B, the circuit board 18 may have a hole 43 in which the UV lights source and heat sink are located. Alternatively, the UV light sources may be secured to the bottom surface of the circuit board, as shown in FIG. 7. FIG. 7 shows a cross section view of a UV light source 46 according to embodiments of the present disclosure. As depicted, the UV light source 46 may be secured to the bottom surface of the circuit board 44 by the suspensions 48, i.e., the UV lights source 46 may be surface mounted onto the circuit board 44.

In embodiments, the suspensions 48 may be formed of an adhesive material. In embodiments, the suspensions 48 not only provide mechanical strength to secure the UV light source 46 to the circuit board 44 but also protect the UV light source 46 from the oscillation/vibration. The suspensions 48 may have the spring constants as the suspensions 42. In embodiments, the material and dimension of the suspensions 48 may be determined so that the resonance frequencies $f_x$, $f_y$ and $f_z$ of the suspensions 48 may be offset from the vibrational frequency of the vibrator 38.

In embodiments, the suspensions 48 may electrically couple the UV light source 46 to the circuit board 44, i.e., the suspensions 48 may include electrical wires/traces that electrically connect the US light source 46 to the circuit board 44.

Figure 9:
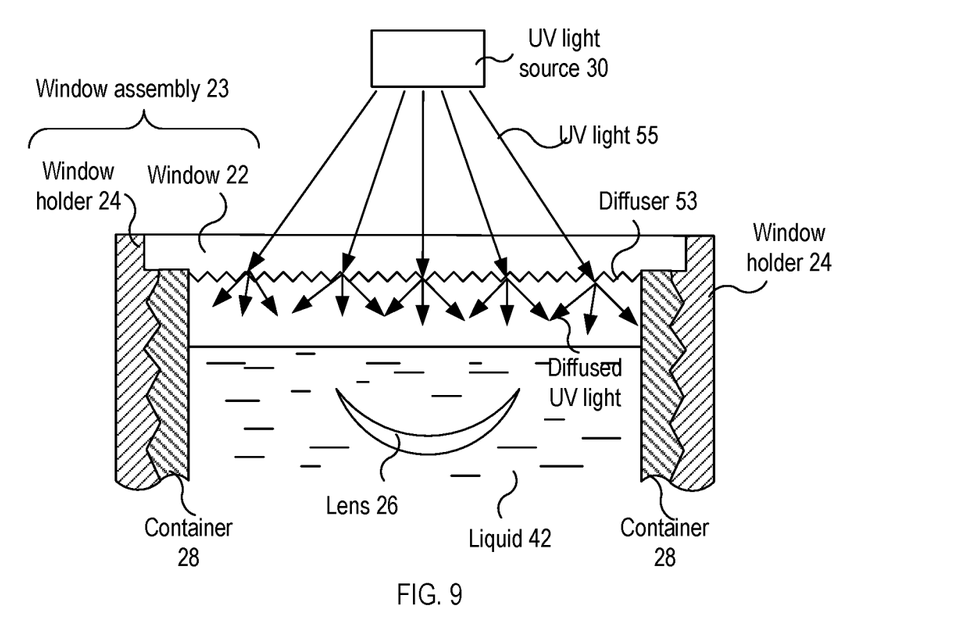
FIG. 9 shows a cross sectional view of a window assembly taken along the direction 9-9 in FIG. 3 according to embodiments of the present disclosure.

As discussed above, the contact lenses may degrade from direct exposure to the UV light over an extended period of time. In embodiments, the UV light source and optical elements may be arranged so that the direct impingement of the UV light on the contact lenses 26 is avoided while most intense part of the UV light is directed to the lens cleaning liquid 42 in the containers 28. FIG. 9 shows a cross sectional view of the window assembly 23, taken along the direction 9-9 in FIG. 3 according to embodiments of the present disclosure. As depicted, the window assembly 23 may include the window 22 and the window holder 24 that is secured to the window, where the window holder 24 may be detachably engaged with the container 28. Unlike the conventional systems that expose the lenses directly to the UV light, in embodiments, to prevent the clouding due to the UV light 55, the window 22 may have a diffusing element (or diffuser) 53 that diffuses the UV light 55. The diffusing element 53 may allow most of the UV light 55 to pass therethrough so that contaminants in the liquid 42 are disinfected by the diffused UV light, but the light intensity on the lens 26 may not exceed a threshold limit so that the clouding of the lens 26 can be prevented. It is noted that the intensity of the UV light 55 may be strongest at the central portion thereof. As such, if the diffuser 53 were not used, the lens 26 may be exposed to direct impingement of the strongest portion of UV light, resulting in lens clouding or discoloration.

In embodiments, the diffusing element 53 may be generated by making a suitable pattern, such as triangular grooves, arrays of dimples or other geometric or random scattering elements, on the window surface so that the diffused UV light is uniformly distributed over the entire liquid 42 in the container 28. In embodiments, the pattern may cover only a portion of the window, specifically aimed at reducing the direct-incidence intensity of UV LED light on the contact lens. In embodiments, the inner surface of the container 28 may be formed of material that reflects the UV light.

Figure 10:
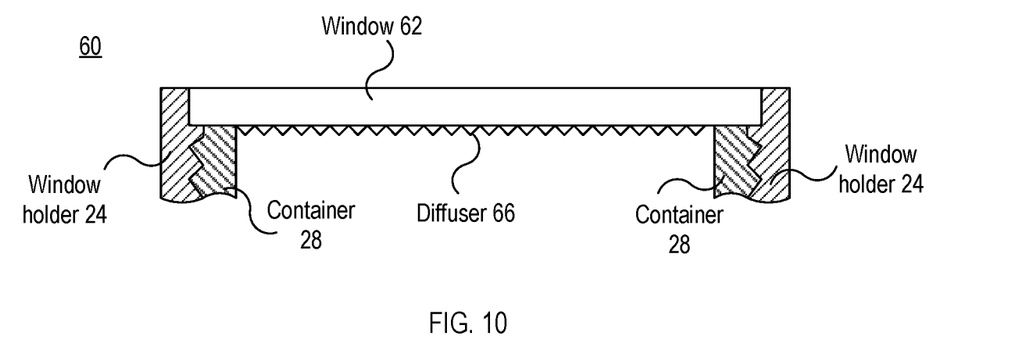
FIG. 10 shows a cross sectional view of a window assembly according to embodiments of the present disclosure.

FIG. 10 shows a cross sectional view of a window assembly 60 according to embodiments of the present disclosure. As depicted, the window assembly 60 may be similar to the window assembly 52, with the difference that a diffuser 66 may be a patterned layer and attached to the bottom surface of the window 62. In embodiments, the diffuser 66 may be formed of material transparent to the UV light and may have a suitable pattern to distribute the diffused light uniformly over the liquid in the container 28. In embodiments, the inner surface of the container 28 may be formed of material that reflects the UV light.

In embodiments, the window 22 may be formed of partially transmissive material so that only a portion of the UV light 55 passes through the window. The window maybe partially transmissive over its entire area, or only in selected areas such as the portion directly under the LED. In embodiments, the diffuser 66 may be formed of partially transmissive material so that only a portion of the UV light passes through the diffuser. The partially transmissive window and/or diffuser may reduce the UV intensity on the lens, to thereby reduce lens clouding or discoloration.

Figure 11:
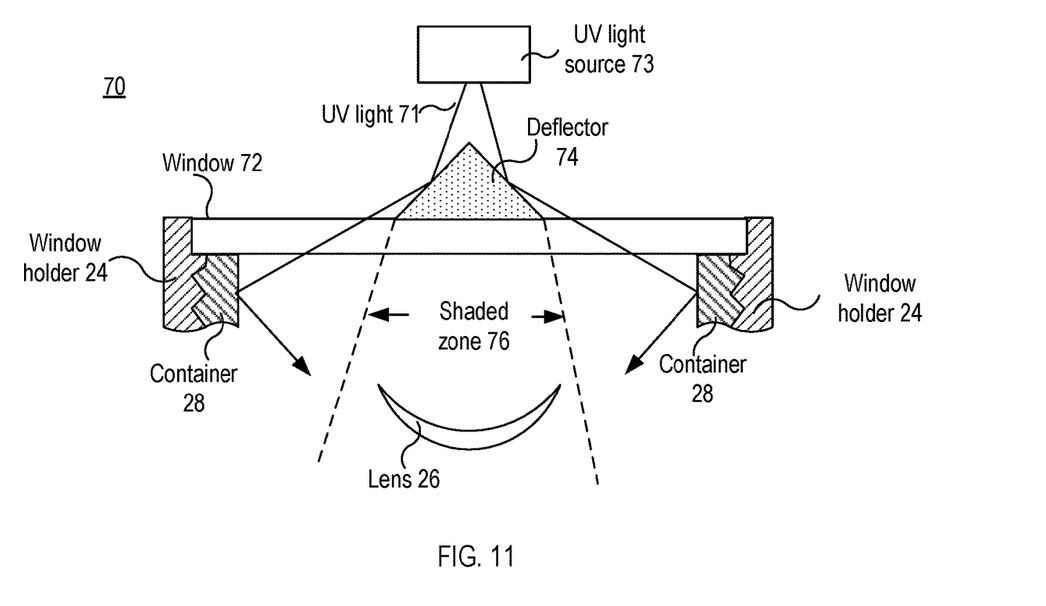
FIG. 11 shows a cross sectional view of a window assembly according to embodiments of the present disclosure.

FIG. 11 shows a cross sectional view of a window assembly 70 according to embodiments of the present disclosure. As depicted, the window assembly 70 may be similar to the window assembly 60, with the differences that a light deflector 74 may be used to redirect the UV light 71 and the window 72 does not have a diffuser. In embodiments, the deflector 74 may have a conical surface that reflects the UV light 71 and the base of the deflector 74 may be dimensioned so that the lens 26 may be located in the shaded zone 76 generated by the deflector. The shaded region refers to the area where the UV light 71 from the UV light source 73 does not directly reach. Since the deflector 74 may prevent the UV light 71 from directly impinging onto the lens 26, the clouding of the lens may be prevented. In embodiments, the inner surface of the container 28 may be formed of material that reflects the UV light. Most of the UV light deflected by the deflector 74 may pass through the window 72 and disinfect the deposits in the liquid.

Figure 12:
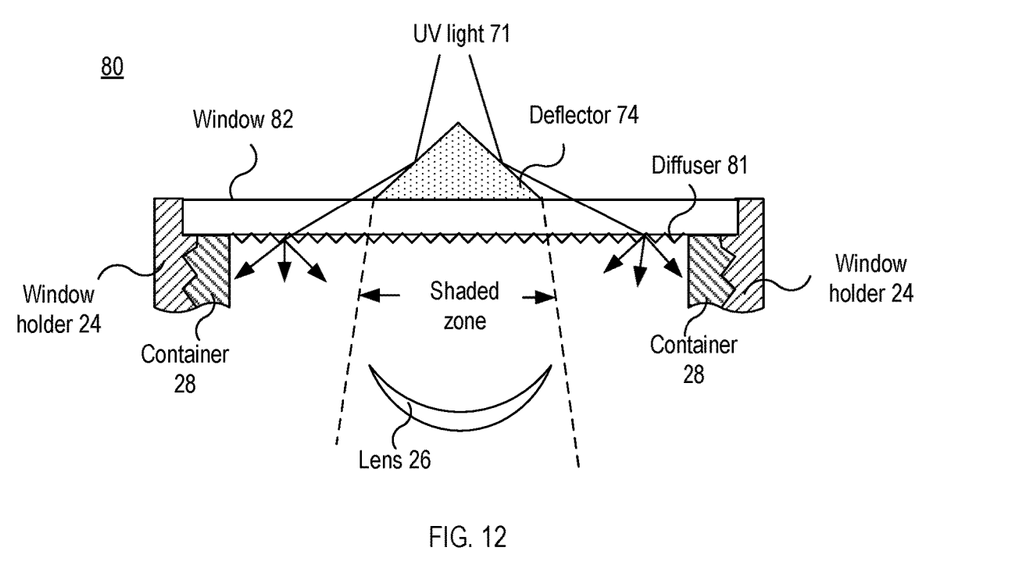
FIG. 12 shows a cross sectional view of a window assembly according to embodiments of the present disclosure.

FIG. 12 shows a cross sectional view of a window assembly 80 according to embodiments of the present disclosure. As depicted, the window assembly 80 may be similar to the window assembly 70, with the difference that a diffuser 81 may be formed on the bottom surface of the window 82. In embodiments, the diffuser 81 may be generated by making a suitable pattern, such as triangular grooves, on the window surface. In embodiments, the diffuser 81 may be a patterned layer and attached to the bottom surface of the window 82. In embodiments, the diffuser 81 may be formed of material transparent to the UV light and have the similar function as the diffuser 53 (or 66). In embodiments, the diffuser 81 may be formed of material that is partially transparent to the UV light.

Figure 13:
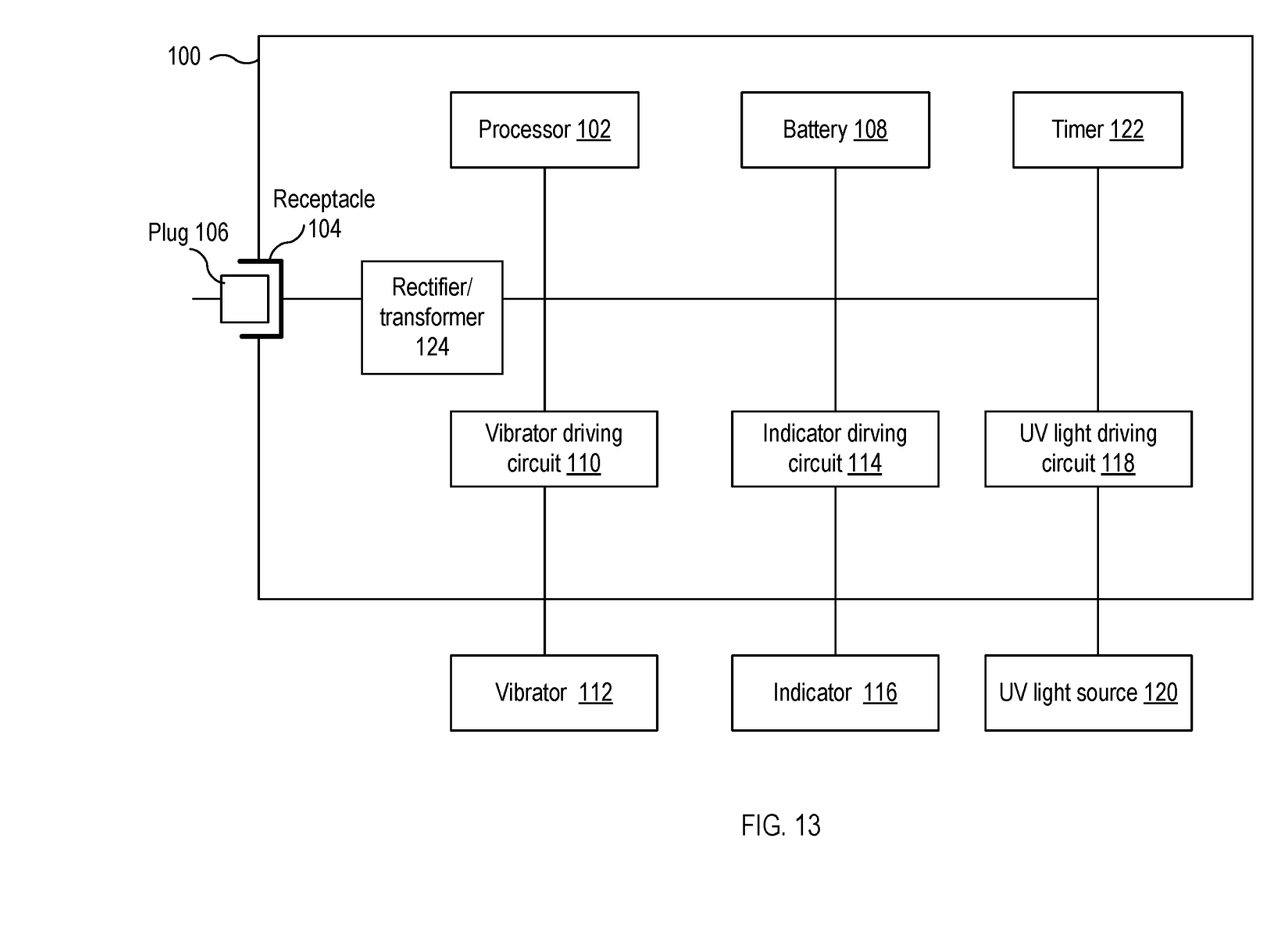
FIG. 13 shows a schematic diagram of a circuit board according to embodiments of the present disclosure.

FIG. 13 shows a schematic diagram of a circuit board 100 according to the embodiments of the present disclosure. As depicted, the circuit board 100 may be similar to the circuit board 18 in FIG. 2 and include various electrical components and circuits, where each of the components and circuits may be hardware, software, firmware or combination thereof. In embodiments, the receptacle 104 (or 36) may receive the power plug 106 that provides electrical power to the circuit board. The rectifier 124 may convert the AC input to a stable DC voltage that may be stored in the battery 108 (or 32) and used by other components in the circuit board. In embodiments, if the power plug 106 provides DC input, a step-down power transformer may be used in place of the rectifier 124.

The processor 102, which may be a microprocessor, may control the operation of the components in the circuit board 100. In embodiments, the vibration driving circuit 110 may control the operation of the vibrator 112 (or 38) that generates oscillation or vibration to induce whirlpool waves in the containers. The turbulent waves may rinse through, clean, and dislodge deposits from the lenses.

In embodiments, the indicator driving circuit 114 may control the indicator 116 (or 15) to provide the current status of the device, such as "ready" or "cleaning", to the user. In embodiments, the indicator 116 may operate as a turn on/off switch or a button for controlling the cleaning cycle. In such a case, the indicator driving circuit 114 may monitor the user's touch on the indicator 116 and communicate with the processor 102 to perform the operations that the user intends to perform.

In embodiments, the UV light driving circuit 118 may control the UV light source 120 (or 30, 33, 46 or 73) to turn on/off the UV light source. In embodiments, the UV lights driving circuit 118 may be included in the circuit board 100 and electrically coupled to the UV light source 120 via a wire(s) included in the suspensions 42 (48 or 49). In alternative embodiments, the UV light driving circuit 118 and the UV light source 120 may be formed in one integral body and protected from oscillation/vibration by the suspensions 42 (48 or 49). In embodiments, the timer 122 may time various operational processes, such as the cycles of the vibrator 112 and UV light source 120, to thereby control the operation of the device.

While the invention is susceptible to various modifications and alternative forms, specific examples thereof have been shown in the drawings and are herein described in detail. It should be understood, however, that the invention is not to be limited to the particular forms disclosed, but to the contrary, the invention is to cover all modifications, equivalents, and alternatives falling within the scope of the appended claims.

What is claimed is:

1. A device for cleaning a contact lens, comprising:
   a container having a chamber for holding a volume of fluid therein;
   a vibration generator for generating an oscillatory motion on the container, the oscillatory motion inducing turbulence in the volume of fluid with sufficient force and duration to dislodge deposits from a contact lens immersed in the volume of fluid;
   a light source for generating radiation to disinfect the dislodged deposits in the fluid and disposed over the container during operation;
   a board member having electronic circuits for controlling the vibration generator and light source and including at least one hole in which the light source is located; and
   a suspension having a first end secured to the light source and a second end secured to the board member to suspendedly secure the light source to the board member, a resonance frequency of the suspension being different from a frequency of the oscillatory motion so that an intensity of an oscillatory motion transferred from the board member to the light source through the suspension is reduced.

2. The device of claim 1, wherein the light source is an ultraviolet light emitting diode (UV LED).

3. The device of claim 2, wherein a wavelength of the radiation ranges from 250 nm to 300 nm.

4. The device of claim 1, wherein the light source generates the radiation in a continuous mode.

5. The device of claim 1, further comprising:
   a window assembly including a window and a window holder and detachably secured to the container to form an enclosed space for the fluid, the window being formed of material that is transparent to the radiation.

6. The device of claim 5, wherein the window has a diffusing element that diffuses the radiation.

7. The device of claim 6, wherein the diffusing element is a pattern formed on at least some portion of one surface of the window.

8. The device of claim 6, wherein the diffusing element is a diffuser attached to a surface of the window.

9. The device of claim 6, wherein the diffusing element partially transmits the radiation.

10. The device of claim 5, further comprising:
    a deflector disposed on the window and preventing the radiation from directly impinging on the contact lens.

11. The device of claim 10, wherein the deflector has a conical surface that reflects the radiation and the container has an inner surface formed of material that reflects the radiation.

12. The device of claim 1, further comprising:
    a heat sink attached to the light source and configured to extract heat energy from the light source.

13. The device of claim 1, wherein the suspension includes a wire for electrically connecting the light source to the board member.

* * * * *